United States Patent [19]
Gardetto et al.

[11] Patent Number: 5,965,433
[45] Date of Patent: Oct. 12, 1999

[54] PORTABLE PERFUSION/OXYGENATION MODULE HAVING MECHANICALLY LINKED DUAL PUMPS AND MECHANICALLY ACTUATED FLOW CONTROL FOR PULSATILE CYCLING OF OXYGENATED PERFUSATE

[75] Inventors: William W. Gardetto, Bedford; John K. Heacox, Mesquite; James L. Matthews, Dallas, all of Tex.

[73] Assignee: Trans D.A.T.A. Service, Inc., Houston, Tex.

[21] Appl. No.: 08/652,696

[22] Filed: May 29, 1996

[51] Int. Cl.$^6$ .................................................. C12M 3/00
[52] U.S. Cl. .................................. 435/284.1; 435/286.6; 422/48
[58] Field of Search .......................... 435/284.1, 286.1, 435/286.6; 422/44, 45, 48

[56] References Cited

U.S. PATENT DOCUMENTS

| | | | |
|---|---|---|---|
| 3,406,531 | 10/1968 | Swenson et al. | 62/306 |
| 3,632,473 | 1/1972 | Belzer et al. | 195/1.7 |
| 3,639,084 | 2/1972 | Goldhaber | 417/394 |
| 3,877,843 | 4/1975 | Fischel | 417/394 |
| 3,881,990 | 5/1975 | Burton et al. | 195/1.7 |
| 3,892,628 | 7/1975 | Thorne et al. | 195/1.7 |
| 3,914,954 | 10/1975 | Doerig | 62/306 |
| 3,935,065 | 1/1976 | Doerig | 195/1.7 |
| 5,051,352 | 9/1991 | Martindale | 435/1 |
| 5,285,657 | 2/1994 | Bacchi et al. | 62/457.9 |
| 5,326,706 | 7/1994 | Yland et al. | 435/283 |
| 5,338,662 | 8/1994 | Sadri | 435/1 |
| 5,356,771 | 10/1994 | O'Dell | 435/1 |
| 5,362,622 | 11/1994 | O'Dell et al. | 435/1 |
| 5,385,821 | 1/1995 | O'Dell et al. | 435/1 |

*Primary Examiner*—David A. Redding
*Attorney, Agent, or Firm*—James L. Jackson; Mayor, Day, Caldwell and Keeton, L.L.P.

[57] ABSTRACT

A portable perfusion/oxygenation module includes respiratory gas driven dual positive displacement pumps coupled to a stacked membrane oxygenator unit for perfusion fluid oxygenation, a valving manifold to control perfusate flow-direction coupled to an organ chamber designed to enable easy installation of organ and maintenance of intra and extra organ fluid pressure. All of the components and oxygen cylinders are fitted into an insulated chest capable of sustaining perfusion and oxygenation for 24 hours. The perfusion/oxygenation apparatus requires no electrical power, is compact with the total weight including the perfusion fluids and organ weighing less than 50 pounds. With low cumulative weight and the extremely low flow rate of gas required to pump the perfusate, the oxygen supply is capable of sustaining pumping operation for 24 hours without gas cylinder change. The dual pumps have axially aligned, commonly connected pistons using adjustable linkages that provide a simple and robust means of adjusting perfusate volume and pumping rate. No movable membranes, diaphragms or electrical power are required to deliver oxygenated perfusate.

12 Claims, 5 Drawing Sheets

PORTABLE PERFUSION/OXYGENATION MODULE HAVING MECHANICALLY LINKED DUAL PUMPS AND MECHANICALLY ACTUATED FLOW CONTROL FOR PULSATILE CYCLING OF OXYGENATED PERFUSATE

FIELD OF THE INVENTION

The present invention is related generally to organ preservation, and in particular to highly portable, non-electric perfusion apparatus for administering a chilled, oxygenated nutrient solution through the vascular bed of an organ following excision of the organ.

BACKGROUND OF THE INVENTION

The ability to maintain organs by gravity-fed oxygenated perfusion fluids was described as early as 1907 by Locke. Perfusion of oxygenated, balanced salt solutions containing sugars to meet energy requirements was shown to be superior to earlier perfusion systems where no sugars nor oxygenation was employed. Living hearts have been maintained viable for 24 hours using those early systems. Preservation of hearts for subsequent transplantation into a recipient animal was also described in literature in 1960 as was the benefit of chilling the organs to 4° C. in the storage condition.

The art and science of organ transplantation has developed rapidly since 1960, due largely to improved methods of suppressing immune rejection of the transplanted organ by the transplant recipient. Presently, donor organs are collected under sterile conditions and are transported to the operating room of a designated base facility where the transplant recipient is standing by. Transportation of the organ is done using portable insulated containers kept at 4° C. by blocks of ice, the organ itself being suspended in a container bathed by the balanced, chilled solution. However, perfusion of fluid through the vessels or cavities of the organ is not practiced nor is oxygenation of the solutions, although the value of such procedures is established and widely recognized. Failure to apply these preferred methods is due to the excess quantity of oxygen required to circulate oxygenated fluid through the pressure dependent perfusion pumps.

Practical use of oxygenated perfusion requires that the organ transport apparatus be self-contained, pump for a minimum of 24 hours and have compact size and low weight so that one person can carry the entire apparatus unassisted. Its size should allow ready transport in standard vehicles such as small cars, helicopters, and jet aircraft. Since fluid oxygenation and organ perfusion are not presently used, the distance between donor and recipient is severely restricted as unperfused hearts progressively deteriorate. Four hours is regarded as the upper limit that a viable organ can be transplanted with a margin of anticipated success.

The ability to transport perfused and oxygenated organs over longer distances and/or for longer times would significantly improve the successful use of donor organs because (1) organs would be in better physiological condition; (2) a larger selection of donor organs might become available; (3) time for better donor matching could influence better organ acceptability; (4) potential recipients might not have to be restricted to a base site; (5) surgical teams could have more predictable scheduling; (6) recipients of better quality organs would likely have a shorter clinical recovery and thus better well-being as well as cost saving; (7) a world-wide network of donors and recipients would be feasible.

The use of perfused, oxygenated and nutrient-balanced salt solutions at a reduced temperature enhances the viability of the transplant organ in several ways: lowering of the perfusion fluid and organ temperature lowers the metabolic activity of the organ's cells and hence reduces the demand for physiologic oxygen levels and consumption of nutrients. Reduction in cell metabolism also reduces the rate of production of by-products of metabolism such as $CO_2$ and lactic acid, thus further reducing tissue damage and stabilizing perfusate pH and osmotic balance. Lowering of the temperature reduces the demand for oxygen and hence protects against inadequate oxygen levels that could result in ischemic tissue. In whole blood perfusate, oxygen transport is enhanced as a consequence of the hemoglobin in red blood cells serving to load, transport, and unload the oxygen in tissues of lower oxygen concentration.

Since perfusion fluids typically do not contain red blood cells, oxygen transportation is a function of the direct solubility of the gas phase (oxygen) in the perfusate solution, also being dependent upon the partial pressure of the gas phase driving gas in the liquid perfusate. Hence, satisfactory oxygen transport is achieved by exposing the perfusate to a gas phase under pressure, the pressure available being limited by the design of the oxygenating chamber and also by the limits of perfusion pressure that can be applied within the vessels of the perfused organ without causing damage. Because of the low oxygen demand of chilled tissue, the solubility of oxygen in water under low partial pressure is adequate to supply cell-tissue needs for maintenance oxygen levels.

DESCRIPTION OF THE PRIOR ART

Hypothermic perfusion devices with oxygenation potential are known in the art and have been shown to work in experimental settings where transport of the apparatus is not needed. None of the conventional models, however, meet the requirements of a transport device that is readily portable and sparing of oxygen consumption. For example, Doerig U.S. Pat. No. 3,914,954 describes an electrically driven apparatus in which the perfusate is exposed to atmosphere thus breaking a sterility barrier, that must be operated upright, and consumes oxygen at high rates and is heavy. Requirement for electrical power in an oxygen-rich container and the availability of portable electrical power limit the practicality of this apparatus.

O'Dell and Gunegin Pat. No. 5,362,622, U.S. Pat. No. 5,385,821 and O'Dell U.S. Pat. No. 5,356,771 describe an organ perfusion system that employs either a fluidic logic device or a gas pressure driven ventilator pump to cyclically deliver gas to a sealed chamber connected to the top of the canister containing the organs. Cyclical delivery of gas under pressure to the upper sealed chamber serves to displace a semi-permeable membrane mounted between the gas chamber and the fluid containing organ canister. Cyclical membrane displacement serves to transduce the gas pressure into fluid displacement on the opposite side, thus providing flow of the perfusate solution.

The membrane is selected for its permeability to gas but not to water, permitting oxygen or other gas mixtures to be driven through the membrane into the perfusate or alternatively to vent $CO_2$ from the perfusate. The intent of such membrane pump devices was to provide a system that used no electricity, used low gas pressure and volumes to achieve perfusate flow, had few moving parts, provided adequate perfusate oxygenation, that could be operated in non-upright positions, that isolated the organ and perfusate from atmosphere, and as a total package, was of compact size and reduced weight to permit portability.

Although these designs have proved functional in experimental settings where portability was not necessary, these membrane pumps failed to meet the criteria claimed by the developers. For example, the transducing permeable membrane requires large volumes of gas to transduce the energy into fluid movement, with each cycle requiring several ml of gas to achieve a fluid displacement of 30–60 ml/stroke. Extrapolation of these performance parameters extended to multiple cycle time periods show that three or more large capacity cylinders would be required to sustain pumping without cylinder replacement for 24 hours. These large capacity cylinders each weigh over 20 lbs and do not satisfy the need for a readily portable system. The membrane pump apparatus is further limited by the gas pressure and volume required to operate a ventilator pump, which is not repairable in the field.

The success of the membrane displacement pump design depends upon the membrane dynamic work being repeatable for multiple cycles without tearing or being displaced from its margins, the results of which would be catastrophic loss of the perfusion function of the device. Available gas permeable membranes are not built to possess elastomeric properties. The apparatus is further compromised by a multiple clamping system for canister lid fixation and sealing, necessary to sustain pressure differential for pumping, consisting of silastic gels, with no design provision to assure against compartment leaks.

The canister flow design attempts to pulse perfusate both within the perfused organ and around the outside of the organ in an attempt to saturate the organ with freshly oxygenated perfusate. This also increases the demand for volumes of oxygen that are needed to saturate the fluid bathing the organ. This procedure has no physiologic basis since the normal routes of tissue oxygenation are achieved by oxygen diffusion outwardly from the organ's vascular bed rather than inwardly through the outer capsule. Since the canister loses $CO_2$, it also loses the added oxygen, the net result being an apparatus whose design is wasteful of transportable gas.

Further, no provisions are made for connecting the donor organ to vessels of various sizes as would be experienced in transporting organs from pediatric to adult clinics. Further, since the perfused organ vessels and the outside of the organ are exposed to pressurized perfusate, the outer pressure resists expansion of the perfused vessels and offers a flow resistance to the perfusate within the vessels. Although this could be regarded as a safety margin against overexpansion of the vessels, it also introduces the danger that smaller vessels and tributaries could be obstructed, thus causing small regions of ischemic tissue.

Since the pulse volume and pressure can be controlled by the pump, introduction of such flow constraints is ill founded. Substitution of a fluidic logic device for a respirator pump does allow less gas/cycle to be used. However, it is restrictive in that typical fluid logic devices are set to operate within defined gas pressure ranges and preclude ready adjustment of flow rates, and being encased valving systems, are not built to allow repair if valving fails.

SUMMARY OF THE INVENTION

The present invention provides an apparatus and method that fulfills these essential criteria, namely, the rate of oxygen utilization allows two 250 liter cylinders to supply at least twenty-four hours of perfusion time, the entire apparatus fits into a standard styrofoam ice chest, is readily portable by one person, uses a simple mechanical drive, and has been shown to maintain human and animal hearts for 18 hours or more with no deleterious effect to the perfused and transplanted organ.

The perfusion apparatus of the present invention utilizes dual positive displacement pumps having pistons interconnected in a push-push configuration. The positive displacement pistons are stroked by pressurized oxygen, with liquid perfusate being pumped through an oxygenator and into the vascular bed of a donor organ during one piston power stroke. Perfusate that drains from the donor organ is collected in a sealed container and returned to the perfusate pump reservoir in response to a power stroke by the other pump.

Pressurized oxygen from a portable supply is alternately directed to the pressurized gas chambers of the first and second pumps by a two port, double-throw flow control valve. The outlet ports of the double-throw control valve are selected by an actuator arm that is mechanically coupled to the commonly connected piston rods of the dual pumps. The supply port is switched between the outlet ports in response to shifting movement of the actuator arm.

The actuator arm is shifted forward and reverse in response to forward and reverse stroking movement of the commonly connected piston rods. The valve actuator arm is engagable by over-center toggle linkage actuators that are spring-biased for rapid shifting movement away from an over-center neutral position in response to forward and reverse piston stroke movement.

According to this arrangement, the two-port, double-throw control valve, dual pistons and over-center toggle linkage operate in a free-running, astable multi-vibrator mode of operation. In this free-running mode, the pistons stroke in a reciprocal push-push arrangement that continuously supplies oxygen to the oxygenator, while slowly discharging perfusate through the oxygenator and into the organ at a first pressure level corresponding approximately to systolic pressure during the first stroke, and then returning spent perfusate collected in the organ container back into the perfusate pump reservoir and into the oxygenator at a second pressure level corresponding approximately to diastolic pressure during the second stroke. Preferably, the inlet oxygen pressure to the pistons is adjusted to provide relatively slow charge and return, with systolic/diastolic pressure strokes cycling in the range of about 1.5 to about 2 strokes per minute.

BRIEF DESCRIPTION OF THE DRAWINGS

The present invention may be better understood and its advantages will be apparent to those skilled in the art by reference to the accompanying drawings wherein like reference numerals refer to like elements in the several figures, and wherein.

DETAILED DESCRIPTION OF THE PREFERRED EMBODIMENT

Figure 1:
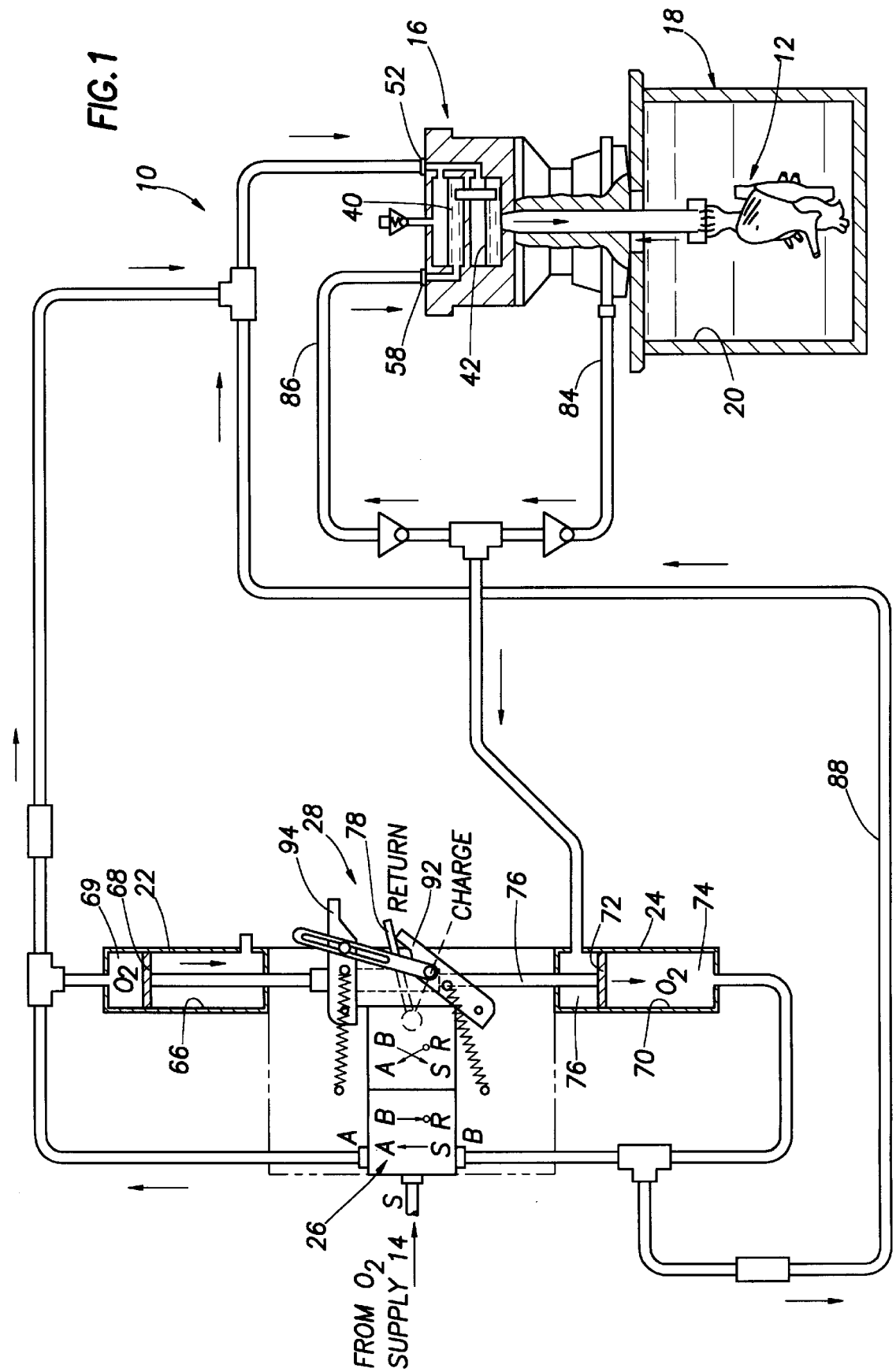
FIG. 1 is a simplified hydraulic circuit diagram showing the interconnection of the principal components of a portable perfusion apparatus of the present invention.
Figure 2:
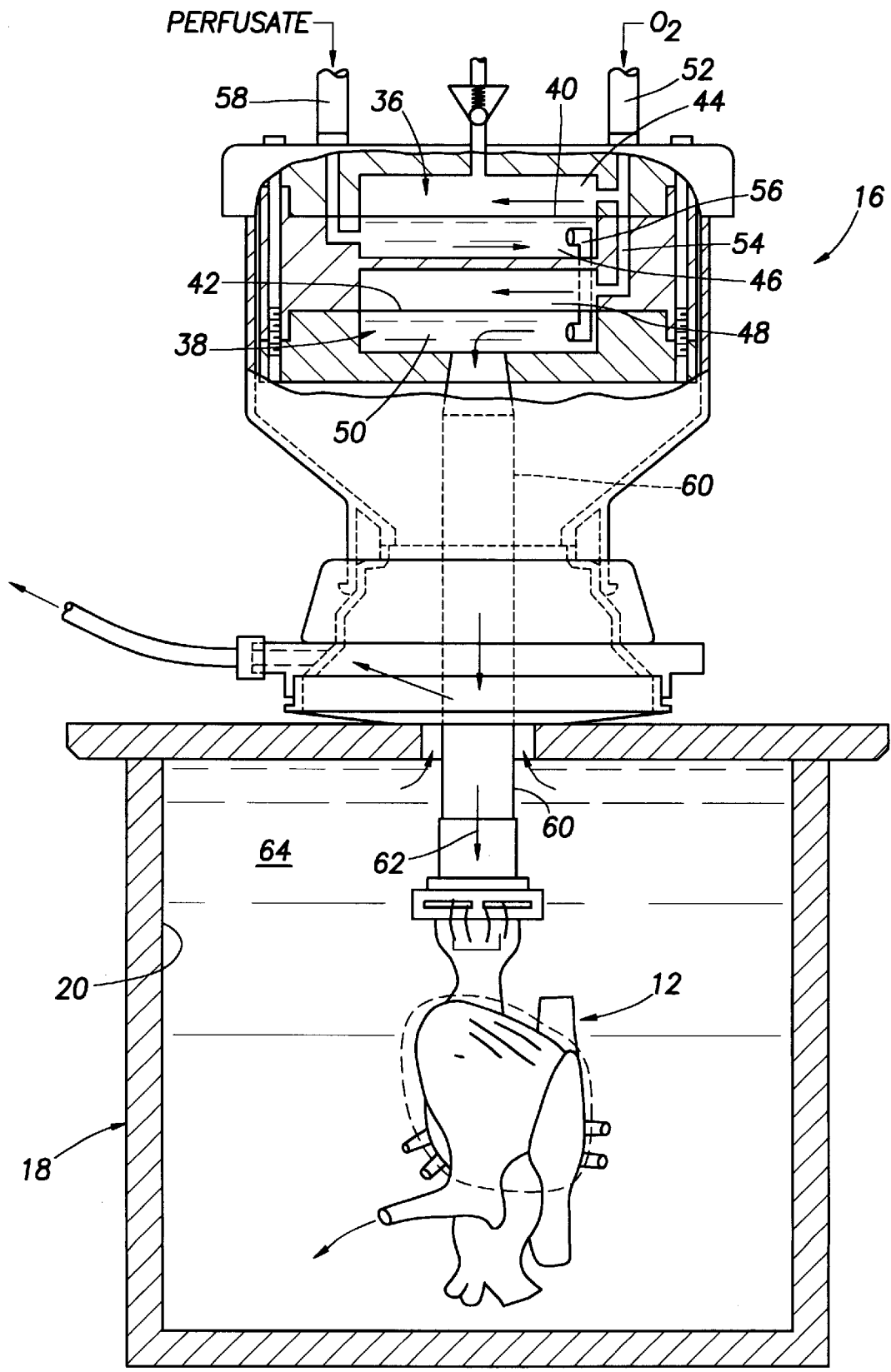
FIG. 2 is an elevational view, partially broken away and partially in section, showing a donor organ suspended within an organ container and coupled to an oxygenator for receiving freshly oxygenated perfusate.
Figure 3:
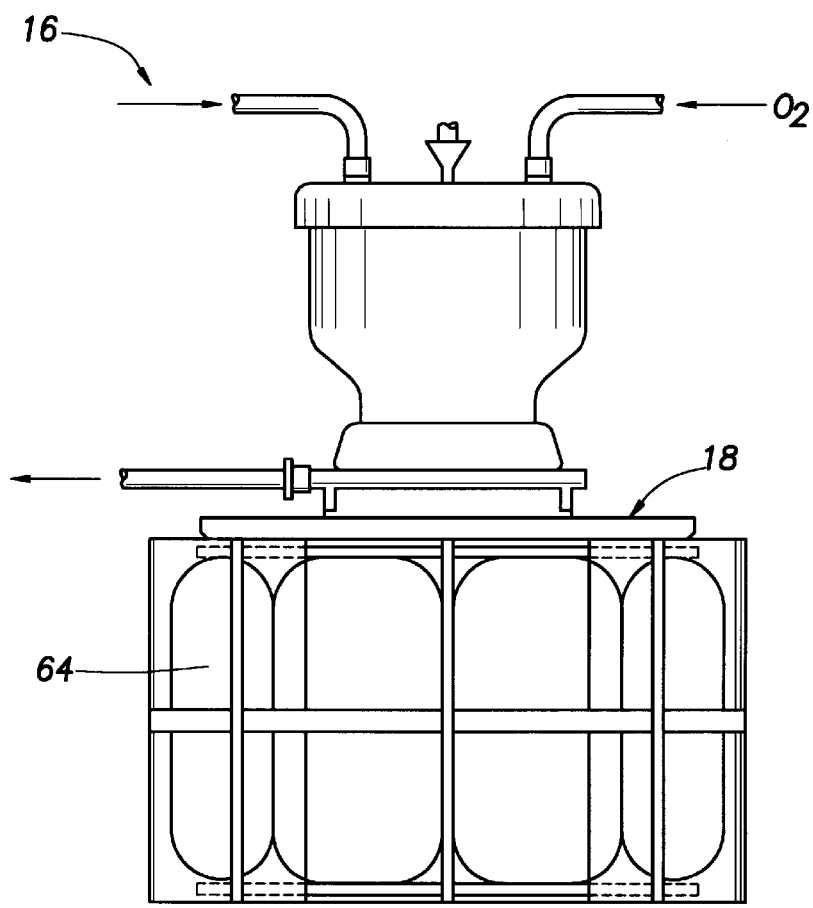
FIG. 3 is a side elevational view thereof, with ice packs surrounding the organ container.
Figure 4:
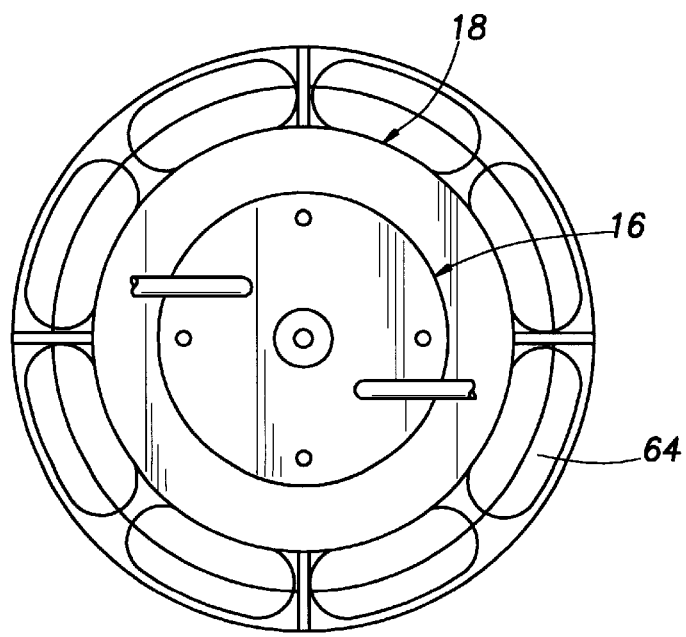
FIG. 4 is a top plan view thereof.
Figure 5:
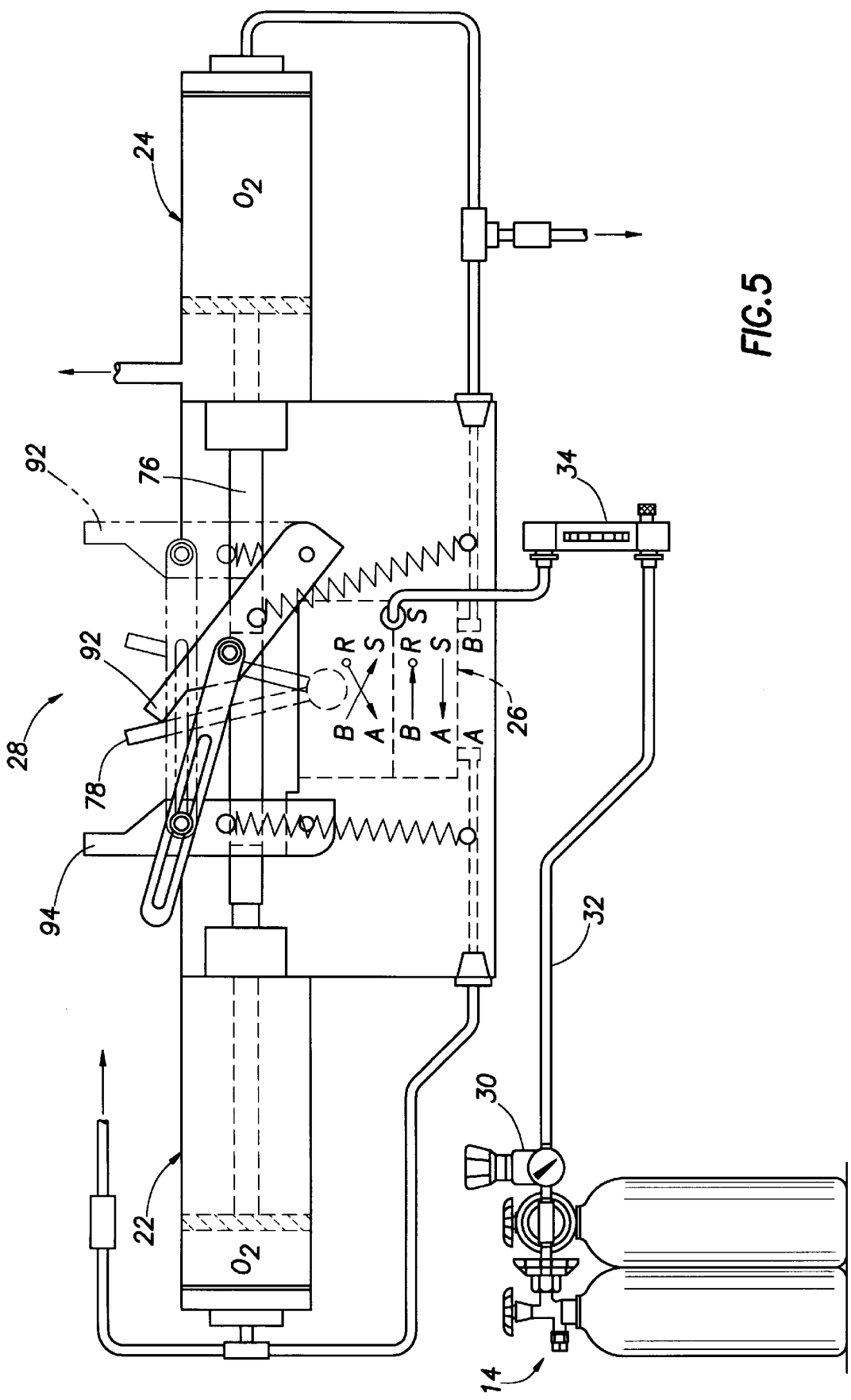
FIG. 5 is a simplified pneumatic and hydraulic diagram which illustrates the interconnection of dual, positive displacement pumps having piston rods commonly connected in a push-push arrangement for charging the oxygenator with perfusate and returning spent perfusate to the primary pump.
Figure 6:
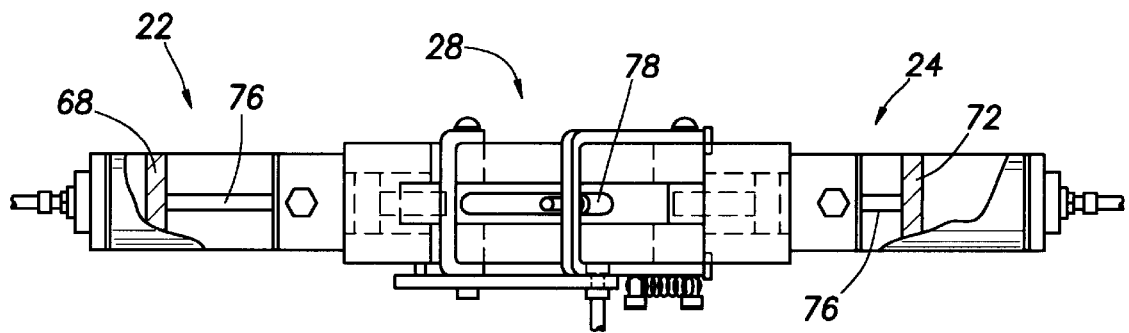
FIG. 6 is a top plan view of the dual pump combination shown in FIG. 5, which illustrates details of a spring-biased, over-center toggle linkage valve actuating apparatus; and, FIG. 7 is a graph illustrating the time variation of systolic and diastolic pressure of oxygenated perfusate that is administered through the vascular bed of the organ shown in FIG. 2.

Referring now to FIG. 1 of the drawings, the combination perfusion/oxygenation apparatus 10 of the present invention provides chilled, oxygenated perfusate at a slow delivery rate for nourishing and conserving a viable, human heart 12. Although the exemplary embodiment features a human heart, other organs that have an identifiable vascular system for carrying blood with separate in-flow and out-flow vessels can be nourished and maintained in a viable condition by the perfusing apparatus of the present invention, for example kidneys, livers, thyroids, lungs, intestines, pancreas, reproductive organs, brains, spleens, as well as severed limbs and the like. The perfusing apparatus 10 can be used for conserving organs and body parts of test animals such as mice, rats, dogs and cats, provided that the vascular in-flow vessel of the animal organ is sufficiently large to attach onto a fluid conduit.

Referring now to FIG. 1, FIG. 2, FIG. 3, FIG. 4 and FIG. 5, the perfusion apparatus 10 of the present invention includes a pair of compressed oxygen cannisters connected in parallel thereby defining a portable oxygen supply 14, an oxygenator assembly 16, an organ container 18 having a sealed chamber 20, a pneumatic actuator 22, a positive displacement pump 24, a flow control valve 26 and a mechanical switching assembly 28 for actuating the control valve 26.

The oxygen supply 14 is coupled to the control valve 26 through a pressure regulator 30, a supply conduit 32 and a float regulator 34. The compressed oxygen supply has a capacity of approximately 450 liters of respirable oxygen.

Compressed oxygen is conducted through the control valve to the pneumatic actuator, the positive displacement pump and the oxygenator. The oxygenator has first and second oxygenator compartments 36, 38 that are divided by first and second oxygen permeable membranes 40, 42, respectively, thereby defining an oxygen chamber 44 and a perfusate chamber 46 in the first oxygenator compartment 36, and defining an oxygen chamber 48 and a perfusate chamber 50 in the second oxygenator compartment 38. The oxygen chambers 44, 48 are connected in flow communication with each other and with an oxygen supply port 52 by a bore 54. The perfusate chambers 46,50 are connected in flow communication with each other by a bypass tube 56. The perfusate chamber is connected in flow communication with a perfusate supply port 58, and the perfusate chamber 50 is connected in flow comunication with the sealed organ chamber 20 through a delivery tube 60. As oxygen flows across the membranes 40, 42, some of the oxygen is transferred across the membranes and is absorbed by the perfusate. The oxygenated perfusate 62 is discharged into the vascular bed of the organ 12, in this instance a human heart, through the aorta and into an artery that bypasses the aorta valve, into the capillary vessels that nourish the heart muscle tissue. The organ chamber is cooled by ice packs 64 that surround the organ container 18.

The pneumatic actuator has a cylindrical bore 66 and a piston 68 that moves axially through the bore, thereby defing a compressed gas chamber 69. Likewise, the pump 24 has a cylindrical bore 70 and a piston 72 that is axially movable through the bore, thereby defining a compressed gas chamber 74 and a perfusate chamber 76. A piston rod 76 connects the pistons 68, 72 together for concurrent stroking movement.

The control valve 26 has a supply port S connnected to the compresed oxygen supply 14 and first and second outlet ports A,B coupled to the compressed gas chambers 69,76 of the pneumatic actuator and the pump 24, respectively. An actuator arm 78 is coupled to the common piston rod 76 for switching the supply port S in flow communication with the first and second control valve outlet ports A,B in response to forward and reverse stroking movement of the commonly connected pistons.

First and second supply conduits 80, 82 connect the outlet ports A,B in flow communication with the compressed gas chambers 69,76 of the pneumatic actuator and the pump, respectively. A supply conduit 82 connects the perfuseate reservoir chamber 76 of the pump in flow communication with the perfusate chamber supply port 58, and a first return conduit 84 connects the sealed organ chamber in flow communication with the perfusate reservoir chamber supply port 52. A second return conduit 86 connects the organ chamber in flow communication with the oxygenator perfusate supply port 58. An oxygen supply conduit 88 and a supply conduit 90 connect the oxygen supply port to the oxygenator.

The present invention provides an apparatus and method that fulfills these essential criteria, namely, the rate of oxygen utilization allows two 250 liter cylinders to supply at least twenty-four hours of perfusion time, the entire apparatus fits into a standard styrofoam ice chest, is readily portable by one person, uses a simple mechanical drive, and has been shown to maintain human and animal hearts for 18 hours or more with no deleterious effect to the perfused and transplanted organ.

The perfusion apparatus 10 of the present invention utilizes dual positive displacement pumps 22, 24 having pistons 68, 72 interconnected in a push-push configuration. The positive displacement pistons are stroked by pressurized oxygen, with liquid perfusate 62 being pumped through an oxygenator 16 and into the vascular bed of a donor organ 12 during one piston power stroke. Perfusate that drains from the donor organ is collected in the sealed chamber 20 of an organ container 18 and returned to the perfusate pump reservoir in response to a power stroke by the other pump.

Pressurized oxygen from a portable supply 14 is alternately directed to the pressurized gas chambers 69, 70 of the first and second pumps 68, 72 by a two port, double-throw flow control valve 26. The outlet ports A, B of the double-throw control valve are selected by a valve actuator arm 78 that is mechanically coupled to the commonly connected piston rods 76A, 76B of the dual pumps. The supply port S is switched between the outlet ports A, B in response to shifting movement of the valve actuator arm 78.

The valve actuator arm 78 is shifted forward and reverse in response to forward and reverse stroking movement of the commonly connected piston rods 76A, 76B. The valve actuator arm is engagable by over-center toggle linkage bails 92, 94 that are spring-biased for rapid shifting movement away from an over-center neutral position in response to forward and reverse piston stroke movement.

Figure 7:
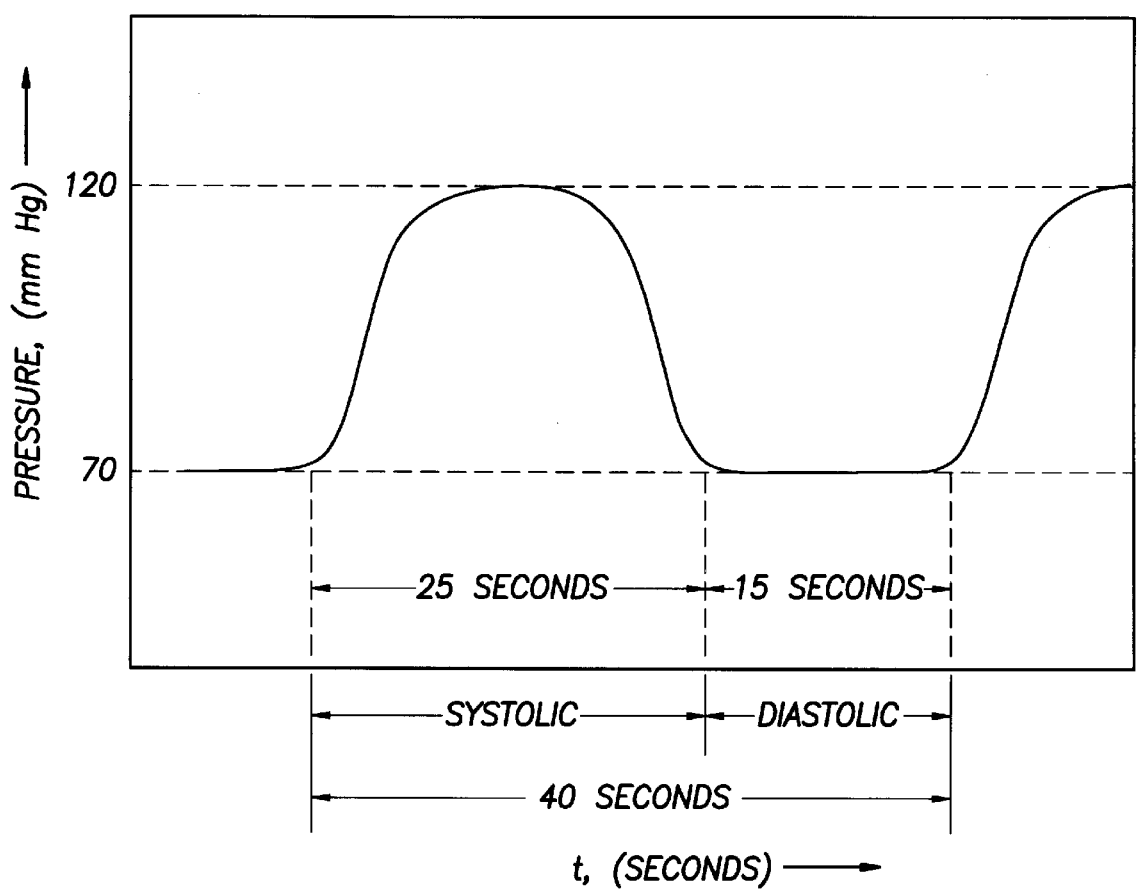

According to this arrangement, the two-port, double-throw control valve 26, dual piston pumps 22, 24 and over-center toggle linkage assembly 28 operate in a free-running, a stable multi-vibrator mode of operation. In this free-running mode, the pistons 68, 72 stroke in a reciprocal push-push arrangement that continuously supplies oxygen to the oxygenator 16, while slowly discharging perfusate 62 through the oxygenator and into the organ 12 at a first pressure level corresponding approximately to systolic pressure during the first stroke (FIG. 7), and then returning spent perfusate collected in the organ container 18 back into the perfusate pump reservoir 76 and into the perfusate chambers 46, 50 of the oxygenator 16 at a second pressure level corresponding approximately to diastolic pressure during the second stroke (FIG. 7). Preferably, the inlet oxygen pressure to the pistons is adjusted to provide relatively slow charge and return, with the systolic pressure stroke lasting about 25 seconds and the diastolic pressure stroke lasting about 15 seconds, providing cycling in the range of from about 1.5 to about 2 strokes per minute.

What is claimed is:

1. Perfusion apparatus of the type including a sealed chamber for administering oxygenated perfusate into an organ, an oxygenator having a perfusate supply port for receiving liquid perfusate and an oxygen supply port for receiving pressurized oxygen;

a positive displacement pump having a compressed gas chamber and a perfusate reservoir chamber separated by a movable piston, a linear actuator having a compressed gas chamber, a piston movable through the compressed gas chamber; a piston rod connecting the pump piston and the actuator piston together for concurrent stroking movement;

a control valve having a supply port for receiving compressed oxygen from a supply and first and second outlet ports coupled to the compressed oxygen chambers of the pneumatic actuator and the perfusate pump, respectively, and an actuator arm coupled to the common piston rod for switching the supply port in flow communication with the first and second outlet control valve outlet ports in response to forward and reverse stroking movement of the commonly connected piston rods, respectively;

first and second supply conduits connecting the first and second control valve outlet ports in flow communication with the oxygen chamber of the oxygenator;

a supply conduit connecting the perfusate reservoir chamber of the pump in flow communication with the perfusate chamber of the oxygenator;

a first return conduit connecting the sealed organ chamber in flow communication with the perfusate reservoir chamber of the pump; and a second return conduit connecting the sealed organ chamber in flow communication with the oxygenator perfusate chamber.

2. Perfusion apparatus of the type having a sealed chamber for receiving an organ and an oxygenator having a perfusate supply port for receiving liquid perfusate, and an oxygen supply port for receiving pressurized oxygen, and a membrane for transferring the oxygen into the liquid perfusate, said oxygenator having first and second oxygenation compartments, the first and second oxygenation compartments being divided by first and second oxygen permeable membranes, respectively, thereby defining a perfusate chamber and an oxygen chamber in each compartment, respectively, wherein the oxygen chambers are connected in flow communication with the oxygen supply port and the perfusate chambers are connected in flow communication with each other, the first perfusate chamber being connected in flow communication with the perfusate supply port and the second perfusate compartment being connected in flow communication with the sealed organ chamber.

3. Perfusion apparatus of the type including a sealed container for perfusing an organ with liquid perfusate solution and an oxygenator having an oxygen chamber and a perfusate chamber for transferring oxygen from a supply of compressed oxygen to the perfusate solution before the perfusate solution is administered to the organ, characterized by: first and second positive displacement pumps each having a compressed gas chamber and a reservoir chamber separated by a movable piston, the pistons of the first and second pumps each having piston rods commonly connected for concurrent stroking movement, a control valve having a supply port, first and second outlet ports and an actuator for selectively directing pressurized oxygen into the compressed gas chambers of the first and second pumps, respectively, in response to shifting movement of the actuator, shifting apparatus coupled between the actuator and the commonly connected pistons for shifting the actuator in the direction of piston stroke movement, first and second power conduits connecting the first and second control valve outlet ports in flow communication with the compressed gas chambers of the first and second pumps, respectively, first and second supply conduits connecting the first and second control valve outlet ports in flow communication with the oxygen chamber of the oxygenator, a first return conduit connecting the oxygenator perfusate in flow communication with the pump perfusate reservoir chamber, and a second return conduit connecting the organ container chamber in flow communication with the pump perfusate reservoir chamber.

4. Self-contained, portable perfusion apparatus comprising, in combination:

a portable supply of compressed gas;

first and second positive displacement pumps, each pump having a cylindrical bore, a piston movable through the cylindrical bore thereby dividing the cylindrical bore into a compressed gas chamber and a perfusate reservoir chamber, and a piston rod attached to the piston and projecting through the reservoir chamber of each pump, respectively, the piston rods being connected together for concurrent stroking movement;

a control valve having a supply port connected to the compressed gas supply, a first outlet port and a second outlet port, and an actuator for switching the supply port in flow communication with the first outlet port in response to shifting movement of the actuator to a first position, and for switching the supply port in flow communication with the second outlet port in response to shifting movement of the actuator to a second position;

shifting apparatus movably coupled to the control valve actuator arm and to the connected piston rods for shifting the actuator in the direction of piston stroking movement;

an organ container having a sealed chamber for receiving an organ;

an oxygenator assembly having an oxygen chamber, a perfusate chamber, an oxygen permeable membrane separating the oxygen chamber and the perfusate chamber, and a delivery tube connecting the perfusate chamber in flow communication with the organ chamber;

first and second power conduits connecting the first and second control valve outlet ports in flow communication with the compressed gas chambers of the first and second pumps, respectively;

first and second supply conduits connecting the first and second control valve outlet ports in flow communication with the oxygen chamber of the oxygenator;

a first return conduit connecting the organ chamber in flow communication with the pump perfusate reservoir chamber; and, a second return conduit connecting the organ chamber of the oxygenator in flow communication with the oxygenator perfusate reservoir chamber.

5. A self-contained, portable perfusion apparatus comprising, in combination:

a portable supply of compressed oxygen;

a sealed chamber for administering oxygenated perfusate into an organ;

an oxygenator having a perfusate supply port for receiving liquid perfusate and an oxygen supply port for receiving compressed oxygen;

a positive displacement pump having a compressed chamber and a perfusate reservoir chamber separated by a movable piston;

a pneumatic actuator having a compressed gas chamber and a piston movable through the compressed gas chamber;

a piston rod connecting the pump piston to the pneumatic actuator piston thereby providing concurrent stroking movement of the pistons;

a control valve having a supply port coupled to the compressed oxygen supply and having first and second outlet ports coupled to the compressed oxygen chambers of the perfusate pump and the pneumatic actuator, respectively, and having an actuator arm coupled to the common piston rod for switching the supply port in flow communication with the first and second control valve outlet ports in response to forward and reverse stroking movement of the commonly connected pistons, respectively;

first and second supply conduits connecting the first and second control valve outlet ports in flow communication with the oxygen chamber of the oxygenator;

a supply conduit connecting the pump perfusate reservoir chamber in flow communication with the oxygenator perfusate chambers;

a first return conduit connecting the sealed organ chamber in flow communication with pump perfusate reservoir chamber; and, a second return conduit connecting the sealed organ chamber in flow communication with the oxygenator perfusate chamber.

6. A self-contained, portable perfusion apparatus comprising, in combination:

a portable supply of compressed oxygen;

a positive displacement pump having a bore, a piston movable through the bore thereby dividing the bore into a compressed gas chamber and a perfusate reservoir chamber;

a pneumatic actuator having a bore and a piston movable through the bore thereby defining a movable boundary for the compressed gas chamber;

a piston rod attached to the pump piston and the actuator piston thereby providing concurrent piston stroking movement;

a control valve having a supply port connected to the portable oxygen supply and having first and second outlet ports coupled to the compressed oxygen chambers of the pneumatic actuator and the perfusate pump; respectively;

the control valve having a actuator arm for switching the supply port in flow communication with the first valve outlet port in response to shifting movement of the actuator arm to a first position, and for switching the supply port in flow communication with the second valve outlet port in response to shifting movement of the actuator arm to a second position;

shifting apparatus movably coupled to the control valve actuator arm and to the common piston rod for shifting the actuator arm to the first position and to the second position in response to forward and reverse stroking movement of the commonly connected pistons, respectively;

a oxygenator having an oxygen chamber, a perfusate chamber and an oxygen permeable membrane for transferring oxygen into the perfusate chamber;

a sealed container for administering oxygenated perfusate into an organ contained within the sealed organ chamber;

power conduits connecting the first and second control valve outlet ports in flow communication with the compressed gas chambers of the pneumatic actuator and perfusate pump, respectively;

supply conduits connecting the first and second valve outlet ports in flow communication with the oxygen chamber of the oxygenator;

a supply conduit connecting the pump perfusate reservoir in flow communication with the oxygenator perfusate chamber; and first and second return conduits connecting the organ chamber in flow communication with the pump perfusate reservoir and the oxygenator perfusate chamber, respectively.

7. Self-contained, portable perfusion apparatus comprising, in combination:

a portable supply of compressed oxygen;

a sealed chamber for administering oxygenated perfusate into an organ;

an oxygenator having perfusate supply port for receiving liquid perfusate and an oxygen supply port for receiving compressed oxygen;

a positive displacement pump having a compressed gas chamber and a perfusate reservoir chamber separated by a movable piston;

a pneumatic actuator having a compressed gas chamber and vent chamber separated by a movable piston;

the pump piston and the actuator piston having piston rods connected together for concurrent stroking movement;

a control valve having a supply port for receiving compressed oxygen from the portable supply and first and second outlet ports coupled to the compressed oxygen chamber of the pneumatic actuator and the perfusate pump, respectively, and an actuator arm coupled to the commonly connected piston rods for switching the supply port in flow communication with the first and second control valve outlet ports in response to forward and reverse stroking movement of the commonly connected piston rods, respectively;

first and second supply conduits connecting the first and second control valve outlet ports in flow communication with the oxygen chamber of the oxygenator;

a supply conduit connecting the pump reservoir chamber in flow communication with the oxygenator perfusate chamber;

a first return conduit connecting the sealed organ chamber in flow communication with the pump reservoir chamber; and a second return conduit connecting the sealed organ chamber in flow communication with the oxygenator perfusate chamber.

8. A self-contained, portable perfusion apparatus comprising, in combination:

a portable supply of compressed gas;

a positive displacement pump having a cylindrical bore, a piston movable through the cylindrical bore thereby dividing the cylindrical bore into compressed gas chamber and a perfusate reservoir chamber, and a piston rod attached to the piston and projecting out of the perfusate reservoir chamber;

a linear actuator having a cylindrical bore, a piston movable through the cylindrical bore thereby defining a movable boundary of the compressed gas chamber;

a piston rod attached to the piston and projecting out of the vent chamber;

a piston rod connecting the linear actuator piston to the pump piston for concurrent stroking movement;

a control valve having a supply port connected to the portable oxygen supply and having first and second outlet ports coupled to the compressed oxygen chambers of the linear actuator and pump, respectively;

the control valve having an actuator arm for switching the supply port in flow communication with the first outlet port in response to shifting movement of the actuator to a first position, and for switching the supply port in flow communication with the second outlet port in response to shifting movement of the actuator to a second position;

shifting apparatus movably coupled to the control valve actuator arm and to the common piston rod for shifting the actuator arm to the first position and to the second position in response to forward and reverse stroking movement, respectively;

an oxygenator having an oxygen chamber, a profusate chamber and a membrane for transferring oxygen into the perfusate chamber;

a sealed container for administering oxygenated perfusate into an organ;

power conduits connecting the first and second control valve outlet ports in flow communication with the compressed gas chambers of the linear actuator and the pump, respectively;

supply conduits connecting the first and second control valve outlet ports in flow communication with the oxygenator oxygen chamber;

a supply conduit connecting the pump perfusate reservoir in flow communication with the oxygenator perfusate chamber; and, first and second return conduits connecting the organ chamber in flow communication with the pump perfusate reservoir and the oxygenator perfusate reservoir, respectively.

9. A self-contained, portable organ perfusion apparatus comprising a portable supply of compressed oxygen;

an oxygenator having an oxygen chamber, a perfusate chamber and a membrane separating the oxygen chamber and the perfusate chamber;

a sealed organ container having a chamber for receiving an organ and a volume of liquid perfusate solution;

a positive displacement pump having a compressed oxygen chamber, a perfusate reservoir chamber and a piston separating the oxygen chamber and the perfusate reservoir chamber;

a pneumatic actuator having a compressed oxygen chamber and a piston defining a movable boundary for the compressed oxygen chamber;

a piston rod connecting the actuator piston and the pump piston for concurrent stroking movement;

a control valve having a supply port connected in flow communication with the portable oxygen supply, first and second outlet ports connected in flow communication with the compressed oxygen chambers of the pneumatic actuator and the perfusate pump, respectively, and a control valve actuator arm for switching the supply port in flow communication with the first outlet port and the second outlet port in response to forward and reverse shifting movement, respectively; and, shifting apparatus coupled to the control valve actuator and to the piston rod for shifting the actuator to the first operating position and to the second operating position in response to forward and reverse stroking movement of the commonly connected pistons, respectively.

10. A self-contained, portable organ perfusion apparatus as defined in claim 9, the shifting apparatus including:

over-centered toggle linkage movably coupled to the actuator arm for rapidly shifting the actuator arm in response to stroking movement of the commonly connected pistons.

11. A self-contained, portable organ perfusion apparatus as defined in claim 9, said oxygenator having first and second oxygenation compartments, the first and second oxygenation compartments being divided by first and second oxygen permeable membranes, respectively, thereby defining a perfusate chamber and an oxygen chamber in each compartment, respectively, the oxygen chambers being connected in flow communication with the oxygen supply port and the perfusate chambers being connected to receive liquid perfusate from the pump reservoir during a charging stroke of the commonly connected pistons, and the perfusate chambers of the oxygenator being coupled to the sealed organ chamber in response to a return stroke of the commonly connected pistons.

12. A self-contained, portable organ perfusion apparatus as defined in claim 11, the over-centered toggle linkage comprising first and second bails disposed on opposite sides of the actuator arm and being mounted for pivotal movement toward and away from the actuator arm, and including first and second tension springs coupled to the first and second bails for urging the bails to move in the direction of piston stroking movement.

* * * * *